Aug. 9, 1949. J. DE GRAAFF Plant Pat. 862
LILY PLANT
Filed Sept. 3, 1947
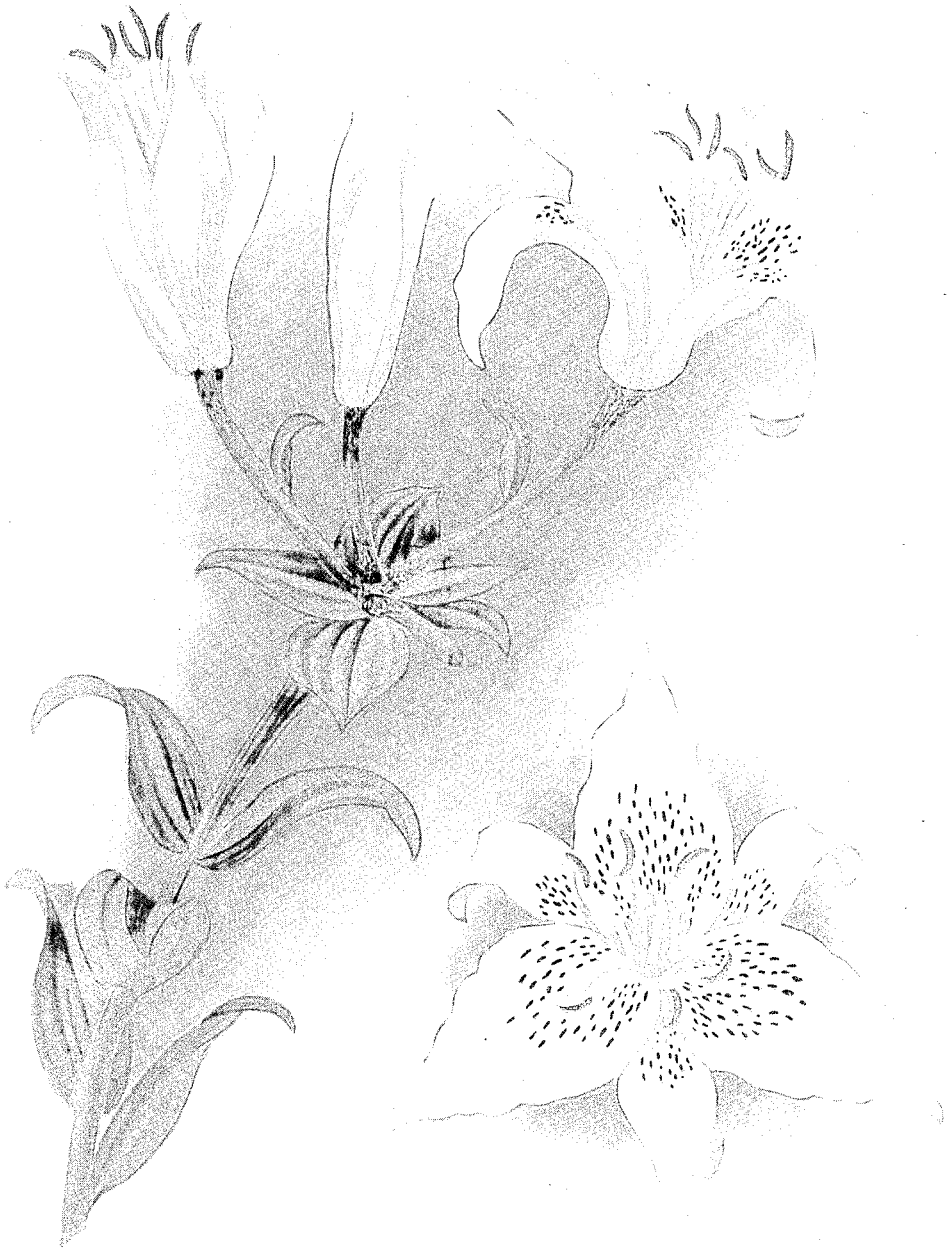
WITNESS
Addison F. Avery
INVENTOR
Jan de Graaff
by John H. Leonard
his ATTY.

Patented Aug. 9, 1949

Plant Pat. 862

UNITED STATES PATENT OFFICE

862

LILY PLANT

Jan de Graaff, Sandy, Oreg.

Application September 3, 1947, Serial No. 771,857

1 Claim. (Cl. 47—60)

This invention relates to a lily plant and particularly to an interspecific hybrid lily plant.

The seed parent of the present lily plant was an unnamed fertile hybrid seedling resulting from the crossing of a *Lilium tigrinum* and a *Lilium umbellatum*. The pollen parent was a *Lilium elegans* which is a variety of the lily plant known as "Alice Wilson" and is though to be the result of a cross between the *Lilium dauricum* and a *Lilium concolor* cross.

The plant was first produced by me by crossing the seed and pollen parent and planting several hundred seeds and selecting the present lily plant from among the resultant seedlings.

The plant was asexually reproduced by me from scales, stem bulbils, underground stem bulblets and bulb division.

In the drawing there is illustrated in the left-hand figure a terminal portion of one of the main stems of the plant with the flowers thereon, and so arranged as to show the cycle of blooming from the opening bud to the full-blown flower, one of the flowers and a portion of its stem being omitted for clearness in illustration, and in the right-hand figure a full-blown flower as viewed from the top.

The plant has a heavy cordlike branched basal root with its origin at the circumference of the basal plate of the bulb. The basal roots are somewhat contractile and the main basal roots are perennial. Stem roots generally emerge from the underground portion of the stem and form a fibrous mass which grows laterally from the stem in all directions. The bulb is a true scaly bulb of the concentric type and reaches about eight to nine inches in circumference, and about two inches in height. Generally the plant flowers from four to five inches in circumference. The roots are medium size and moderately deep with the usual lateral spread.

The resistance of the bulbs and roots to disease and drouth is exceptional and the resistance to wetness is good. They have good winter resistance unprotected and exceptional winter resistance when protected. The roots and bulbs are rather indifferent as to soils.

The exposed portion of the plant is herbaceous, upright and compact with separate stems. It is of the usual size for this type of plant, being from three to four feet in height and ten to sixteen inches in spread. The stem is elongated and bears numerous narrow leaves alternately arranged and disposed at right angles to the stem. The growth of the exposed plant is vigorous and its resistance to low temperature when protected is exceptional as also is its resistance to disease and drouth. It withstands wet seasons well, though it prefers moderate sun with very light shade and any exposure other than north. It thrives well in a heavy to light loam which is well drained. The main stalks are upright, herbaceous, stiff and tough and are generally adequate to support the foliage and bloom well.

The color of the new growth could be termed bright grass green, whereas the older growth is a darker green. On the average they are comparable to parrot green of Maerz and Paul Plate 21–L–6. The color is relatively uniform throughout, though frequently adjacent the flower and at the point of branching from the main stem, the flower stems are speckled with a color comparable to Maerz and Paul Plate 56–L–12, as illustrated in the drawing. The main stems or stalks average from thirty-six to forty-eight inches in length and are smooth, ribbed and naked.

The foliage is compact, the leaves being alternately arranged and abundant. The new leaves are a bright parrot green on top, comparable to Maerz and Paul Plate 21–L–6, and bright grass green with a grayish tinge on the bottom. The older leaves are of somewhat darker green and fairly dull on top and of the same color but with a grayish cast on the bottom. Their color is relatively uniform. They are of medium size, being from three to seven inches in length with a width of one-quarter to three-quarters inches and are of the usual shape for this type of plant. They are of medium thickness with smooth glossy upper faces and smooth under faces with a prominent midrib and their persistency on the plant is excellent.

The plant blooms well throughout the temperate zone, particularly in an even temperature region thereof, and prefers a well drained though moist soil, varying from acid through neutral to slightly alkaline. A rich loam is best for this purpose. For the best results in blooming, a moderately cool temperature and very light shade to full sun are preferred though the direct hot sun is somewhat detrimental, the flowers being slightly smaller under hot dry conditions. The quantity of flowers is determined by the previous year's growth, the maximum being obtained under moderate temperature and full sun with average moisture.

There is a tendency for the color of the older flowers to fade more quickly under hot dry conditions. Fewer flowers generally are borne in shady locations and the flowers are smaller in dry hot locations in the full sun. Under the latter condition the color of the flowers is somewhat lighter. The blooming period varies in different locations, but in the State of Oregon the blooming season begins in late June or early July and lasts from two to three weeks, during which period the plant blooms continuously.

The buds are large and of the usual elongated shape. They are supported in a generally upright position. When the petals begin to unfurl, they are a color which I would designate as a light nasturtium red, and when half-blown, a vivid nasturtium red. As illustrated in the drawing, the main flower color at the lightest portion is comparable to "Indian Orange" of Maerz and Paul Plate 1–D–12 which merges into a color comparable to "Firecracker" of Maerz and Paul Plate 1–H–12 in the darkest portion of the flower. The petals are spotted with brownish black spots. The pistils and stamens are of a color comparable to Maerz and Paul Plate 1–A–11, the anthers being comparable to Maerz and Paul Plate 56–L–12.

The pedicels average from two-and-one-half to four inches and are smooth, shiny and slightly ribbed. In general they could be said to be green overlaid with a slight reddish brown. They have an unusual characteristic in that they support the flowers in a semi-upright position at an angle of about 60° from the ground level.

The plant opens at a medium rate though the rate of opening is slower in cooler cloudy weather.

The flowers are very unusual in shape and size. They average about six to nine inches in diameter and are borne seven to twelve to a plant in racemes. Their permanence on the blooming plant is excellent with flowers lasting from four to seven days. Their permanence when cut is also good, the flowers lasting from three to six days. When in full bloom the petals and flowers are a very vivid, brilliant red, as above described. The lower two-thirds of each petal is sparsely dotted with the brown spots described, the distal one-third of the petals being unspotted. There is a very prominent nectariferous furrow at the base of each petal bordered with numerous papillae. The edges of the petal vary from slightly wavy to gently crimped. The reverse of the petals is in general a red similar to, but not as smooth and bright as, the top of the petals. From a distance the general tonality is the intense vivid red above described which remains relatively uniform throughout the blooming season, though as the flowers age, the red tends to become less pronounced and an orange coloring shows slightly.

The petals are smooth, waxy and heavy. On the inside they appear smooth and glossy each with a center furrow bisecting it longitudinally. They have a papillae bordering furrow at the base of the segments. From the outside they are smooth though not as glossy on the inside and have a pronounced ridge corresponding to the inside furrow. They are generally slightly recurved, tapering to a blunt rounded tip and base with the widest portion extending one-third of the length of the petal from the base. The edges are very slightly crinkled and curled inwardly.

In general appearance the flower is a huge six-pointed semi-upright star shape, the space between adjacent petals being visible the distal two-thirds length of the petals. The flower from the top appears generally flat with slightly recurved petal tips, the edges of the basal portions of the segments slightly overlapping each other. The flower has a faint but pleasant fragrance. Its stamens are simple, with relatively long filaments, there being six stamens in each flower.

The most pronounced characteristics of the plant are the unusual size and shape of the flowers and the manner in which each flower is carried in a semi-upright position of about a 60° angle from the ground level, the non-fading quality of the flowers, the substance and length of the petals or floral segments, the vivid brilliant color of a shade which is unusual in genus Lilium, the bulbils which are borne in the axils of the leaves and which are sparse on the lower portion of the stems and more numerous on the upper portion and which are round, dark brown in color and average from one-fourth to three-eighths inches in diameter. It is noted also that these bulbils are relatively scattered on small plants and they first appear as white raised dots in the leaf axil two or three weeks prior to flowering and mature about the same time as the fruit, a characteristic of bulbil formation which is not possessed, to my knowledge, by any other named variety of this general type or class of lily.

I claim:

The variety of lily plant herein shown and described characterized by the unusual size and shape of the flowers and semi-upright manner in which they are borne, the non-fading quality of the flowers, the substance and length of the petals, the vivid brilliant color of an unusual shade, and the unusual manner in which the bulbils form.

JAN DE GRAAFF.

No references cited.